United States Patent [19]

Gettens et al.

[11] Patent Number: 4,618,861

[45] Date of Patent: Oct. 21, 1986

[54] PASSIVE ACTIVITY MONITOR FOR LIVESTOCK

[75] Inventors: John W. Gettens, Ithaca, N.Y.; Nick A. Sigrimis, Halandri, Greece; Norman R. Scott, Ithaca, N.Y.

[73] Assignee: Cornell Research Foundation, Inc., Ithaca, N.Y.

[21] Appl. No.: 713,946

[22] Filed: Mar. 20, 1985

[51] Int. Cl.[4] .............................................. H04Q 9/00
[52] U.S. Cl. ............................... 340/825.54; 128/903; 340/573; 340/870.38; 119/51 R
[58] Field of Search ...................... 340/825.54, 870.38, 340/573, 505; 128/419 N, 774, 782, 903; 119/51 R; 377/27

[56] References Cited

U.S. PATENT DOCUMENTS

| | | | |
|---|---|---|---|
| 4,232,686 | 11/1980 | Kammlade, Jr. | 340/573 |
| 4,237,900 | 12/1980 | Schulman et al. | 128/903 |
| 4,333,072 | 6/1982 | Beigel | 340/825.54 |
| 4,510,495 | 4/1985 | Sigrimus et al. | 340/825.54 |

*Primary Examiner*—Donald J. Yusko
*Attorney, Agent, or Firm*—Sughrue, Mion, Zinn, Macpeak and Seas

[57] ABSTRACT

An estrus detection system using a transponder mounted to an animal and including a motion sensor. The motion sensor produces a series of pulses as a function of movement. A counting circuit is energized by the sensor. A storage circuit retains the count together with an identification code unique to the animal. The transponder is interrogated to receive data and such is processed to determine estrus.

11 Claims, 8 Drawing Figures

U.S. Patent  Oct. 21, 1986  Sheet 3 of 3  4,618,861
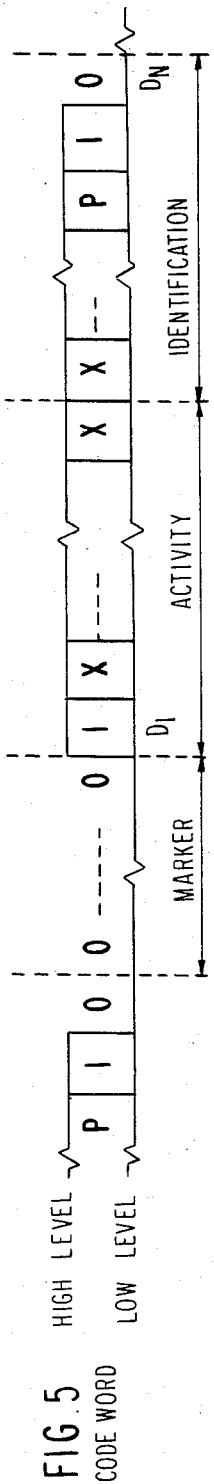
FIG. 5 CODE WORD
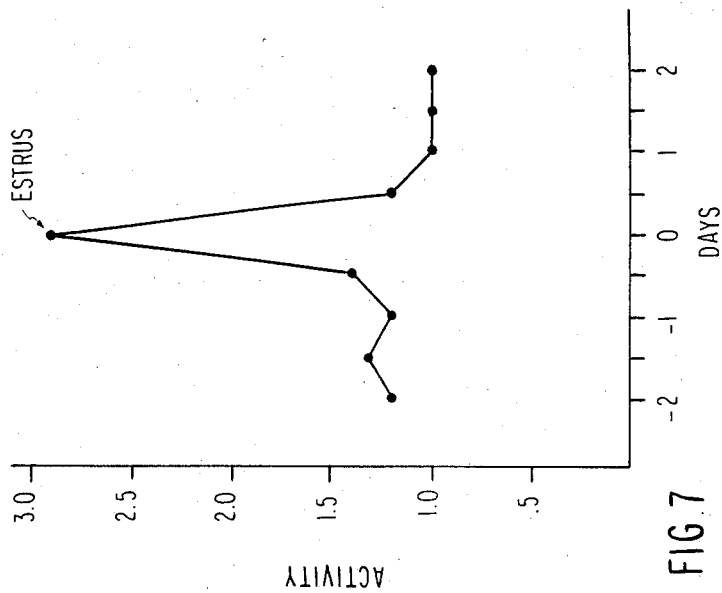
FIG. 7
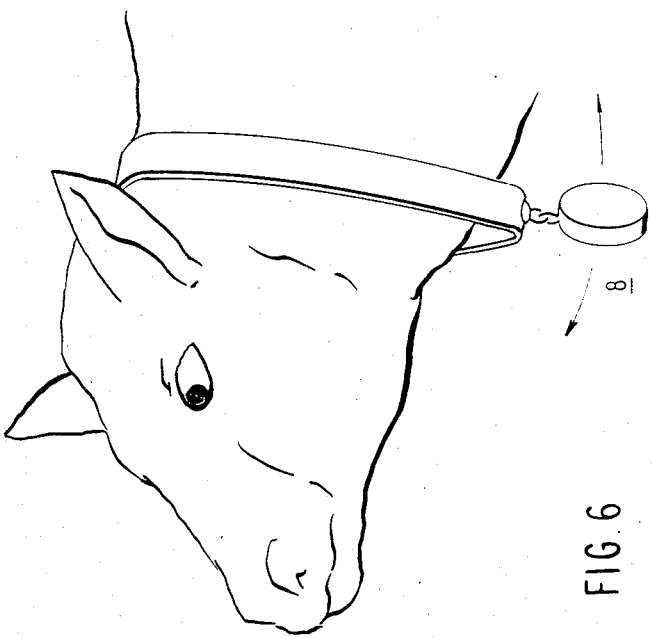
FIG. 6

PASSIVE ACTIVITY MONITOR FOR LIVESTOCK

BACKGROUND OF THE INVENTION

This invention relates to a passive system for the identification of remote movable objects together with a capability of storing and transmitting information uniquely associated with that object. This invention is related to U.S. patent application Ser. No. 406,471, filed Aug. 9, 1982, now U.S. Pat. No. 4,510,495 and entitled "Remote Passive Identification System" now U.S. Pat. No. 4,510,495.

This invention utilizes the identification and transmission aspects of that co-pending application and enhances the system by providing for data collection and storage of parameters unique to the identified object. As in the case of U.S. Pat. No. 4,510,495, this invention has particular utility in livestock management.

Advances in microelectronics have been applied to systems employing coded transponders associated with an object to be identified and engergized by interrogator burst pulses, such that a transmission of coded information signals unique to the object carrying the transponder is generated. Such techniques, when pursued in the dairy industry, allow for efficient herd management by identifying each animal. For example, with cows, once identity has been established, additional data associated with that individual cow may be collected and appropriate action taken. Herd management, therefore, requires in the first instance the identification of the animal such that monitoring of health, reproductive status, allocation and distribution of feed and production (i.e., milk in the case of cows) can all be monitored.

In the context of dairy herds, estrus detection is an important aspect of herd management. Estrus detection rates have a direct influence on the profitability of the herd as a function of calving interval. The optimum calving interval is approximately twelve months. A longer interval results in decreased milk production per cow per day and fewer calves. At present there exists no reliable automated technique of estrus detection on dairy farms. Manual, visual observation and pedometers are typical of attempts based on increased activity of the animal to detect estrus. Those techniques are accurate provided the farmer has sufficient time for observation of the animals. It has been estimated that the present average estrus detection rate is in the range of 40-60%. Given the clear dependency of herd profitability on this detection rate, a need exists for a system employing a reliable estrus detection technique which can be used in the context of contemporary herd management systems.

Reference is made to U.S. Pat. No. 4,247,758. The animal identification and estrus detection system, described therein, employs an activity sensor/recorder, a transponder, an interrogator and an information processing unit. The motion sensor is a mercury switch/battery combination. Motion by the animal wearing the sensor causes the mercury switch to close, which produces a voltage pulse incrementing a binary counter. The sensor defined in U.S. Pat. No. 4,247,758 outputs a voltage pulse of constant amplitude whenever the switch is opened and closed. This constant amplitude pulse is generated independent of force and velocity of motion provided the force is sufficient to close the mercury switch. Consequently, the system cannot detect between various types of motion.

A major disadvantage of the U.S. Pat. No. 4,247,758 system is that it requires a power supply for the sensor and counter. That is, the device carried by the animal is an active device necessitating the use of a battery to power both a sensor and the counter. The requirement of a battery is of considerable importance in application of such devices to animals. For example, a battery operated device must be removed periodically to change batteries which is a potentially arduous task in large herds. The requirement for a battery adds considerable weight and cost to the individual devices. Consequently, a system which eliminates a battery represents an important improvement in this technology. A battery free device may, for example, be implanted in the animal. Even if not implanted, it may remain on the animal over the lifetime of the device or the animal without maintenance.

SUMMARY OF INVENTION

Given the deficiencies of the prior art, it is an object of this invention to define a system capable of identification of an object and detection of dynamic characteristics unique to that object.

Another object of this invention is to define a system which employs a transponder for identifying each object together with an activity monitor coupled to such an identification system.

A further object of this invention is to define a system for herd management having the capability of identifying each animal in a herd and monitoring activity of each animal.

Yet another object of this invention is to define an estrus detection system utilizing a passive transducer not requiring a battery or any other depletable energy source.

These and other objects of this invention are accomplished in an identification system employing passive techniques of information storage and transmission. The system in its most basic components comprises an activity monitor which is used to sense and record motion of the object, typically an animal, under active management. Also carried is a transponder for encoding such activity together with identification information unique to that animal. At a stationary location, typically an entrance to a barn or milking parlor, a transmitter/receiver is stationed to interrogate the transponder and extract from it stored data relative to activity and animal identification. A data processor is employed for conversion, manipulation and storage of such activity and information retrieval. Such is used to determine the onset of estrus by historically monitoring motion or activity of the animal.

This invention will be described in greater detail by referring to the attached drawings and the description of the preferred embodiment which follows.

BRIEF DESCRIPTION OF THE DRAWINGS

FIG. 5 is an illustration of the data format of the code word generated by the transducer;

FIG. 6 is a schematic illustration of an activity monitor and transducer carried by an animal; and FIG. 7 is a graph of Average Activity Level Profile for cows as a function of time.

DESCRIPTION OF THE PREFERRED EMBODIMENT

This invention employs microelectronics in the realm of agriculture and in particular, to automation in the context of dairy herd management. Microelectronic technology, as applied by this invention, allows for active monitoring of herd health, reproductive status, allocating and distributing feed, and monitoring milk production. All of these facets of herd management are directly related to productivity and ultimately profitability of the operation. An essential area of automated dairy herd management is the standing requirement that each animal in the herd be identified. Only when identification is carried out may additional information concerning that animal be properly used so that action, based on such information, can be taken. U.S. Pat. No. 4,510,495, entitled "Remote Passive Identification System" now U.S. Pat. No. 4,510,495 and commonly assigned with this application, discloses an accurate and reliable identification system used in such dairy herd management. The disclosure of U.S. Pat. No. 4,510,495 is incorporated herein by reference since the basic system aspects, vis-a-vis identification per se, are used in this invention. This invention represents an improvement over that basic system, while utilizing the same system architecture, provides additional capabilities in terms of selective information storage and retrieval.

An important aspect of this invention is the gathering of information for the detection of estrus. The detection rates of estrus have a direct influence on herd profitability which is dependent on calving interval. This invention allows for automated accurate identification of estrus in individual animals, wherein at present, detection rates are in the range of 40-60%.

The detection system of this invention determines the onset of estrus by monitoring an animal's motion or activity. In the case of cows, the daily activity of a cow in the dairy herd varies only slightly on a day-to-day basis. Within the herd, however, periods of estrus for an individual cow are signaled by a substantial increase in activity over a non-estrus baseline level for that particular animal. Consequently, by monitoring activity and establishing such baseline data, the onset of estrus can be determined accurately. This invention, therefore, operates to record activity of the animal so that periods of estrus may be differentiated from non-estrus periods. While correlating estrus to increased activity is known per se, techniques of information gathering germane to individual cows in the context of a herd are not known.

Figure 1:
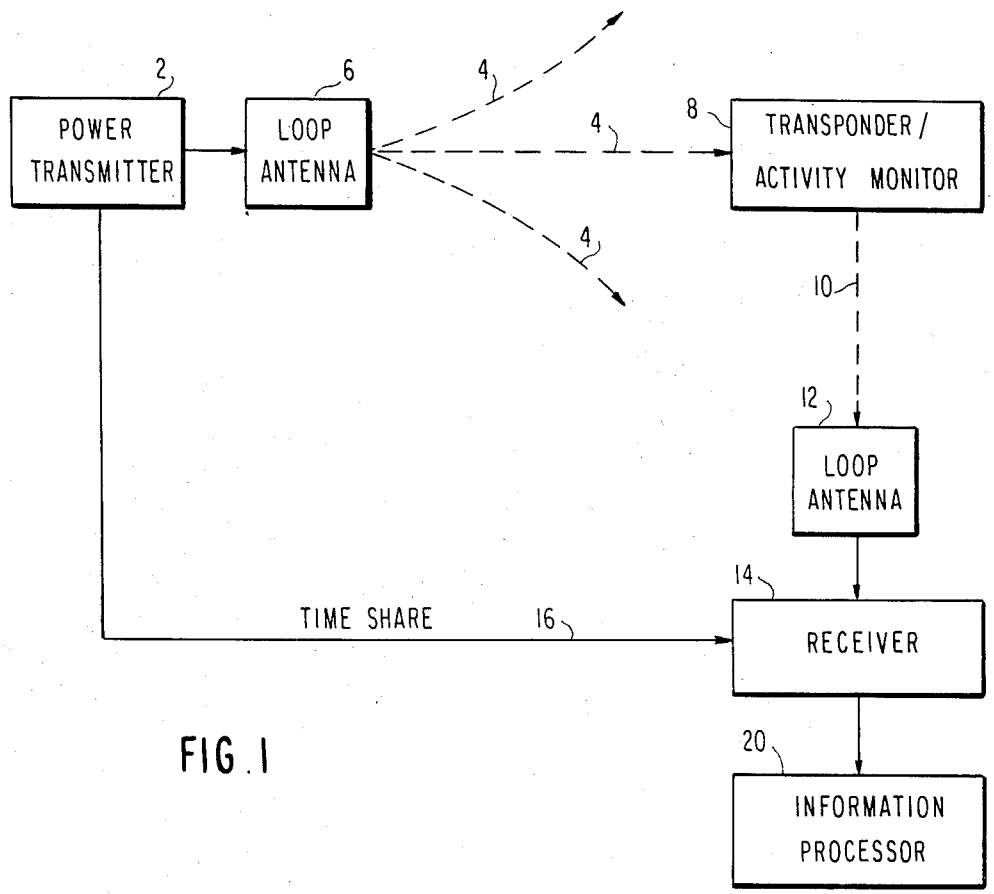
FIG. 1 is a block diagram of a remote passive identification system and information processor in accordance with this invention.

Referring to FIG. 1, the remote passive identification system employing a transponder and activity monitor are depicted in block diagram format.

A power transmitter 2 having an associated loop antenna 6 produces a plurality of RF burst signals 4. As described in the co-pending application, an oscillating field configuration is developed wherein the burst signals are received by the transponder 8. This invention, as will be described herein, integrates an activity monitor with the transponder.

As shown in FIG. 6, the entire transponder/activity monitor is carried by the animal, such as a cow, around the animal's neck wherein it is free to swing along any of the three principal axes, such that motion of the animal is directly transmitted to the activity monitor.

Figure 2:
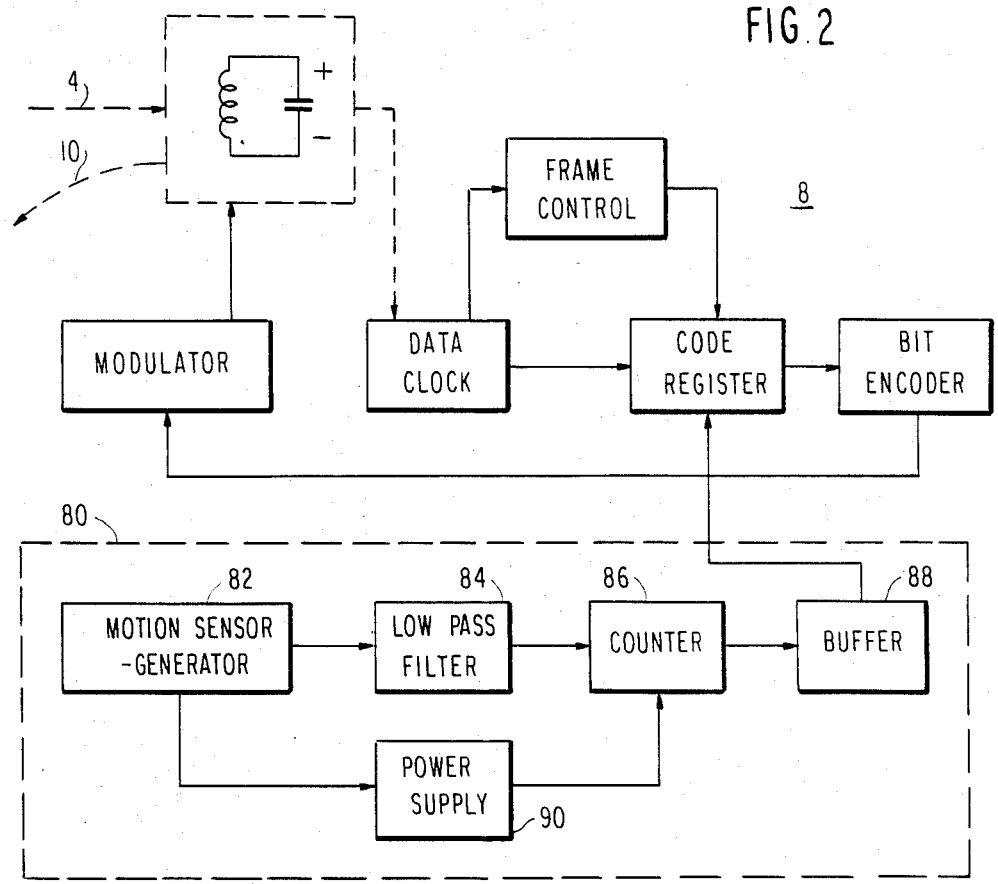
FIG. 2 is a block diagram of the system transponder and activity monitor which is carried by the object to be identified.

Referring to FIG. 2, the combined transponder and activity monitor are illustrated in functional blocks. The transponder portion of FIG. 2 corresponds to the transponder illustrated in the same corresponding figure of U.S. patent application Ser. No. 406,471. The disclosure of that patent application is expressly incorporated herein by reference for description of the operation of that transponder.

In accordance with this invention, an activity monitor 80 is operably coupled to the transponder. In practice, such would be formed as a single circuit, integrated on a common board or chip.

Figure 3A:
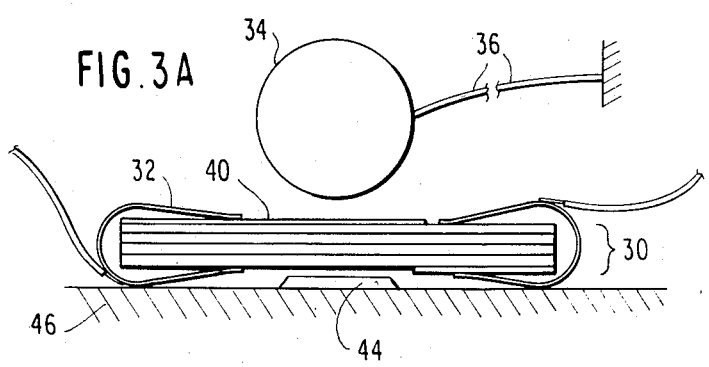
FIG. 3A is a side view of the motion sensor portion of the activity monitor.
Figure 3B:
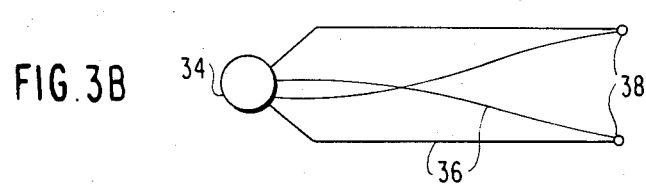
FIG. 3B is a top view of a component of that motion sensor.
Figure 4:
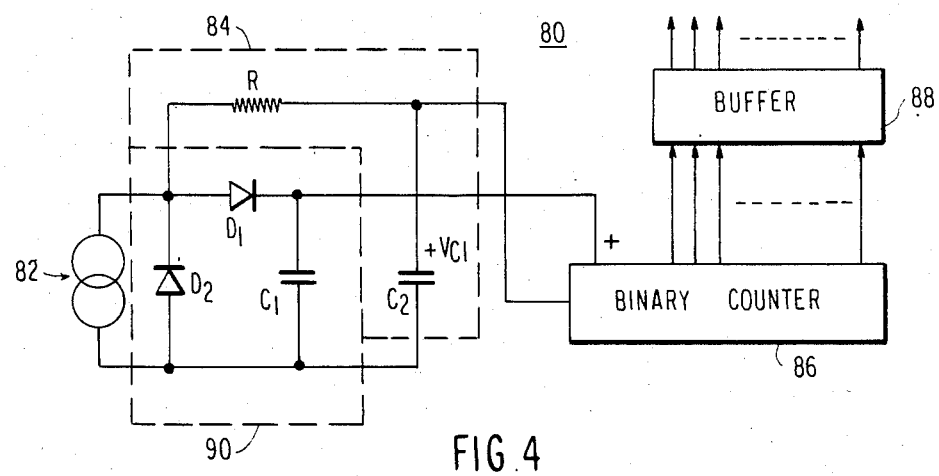
FIG. 4 is a schematic circuit diagram of the activity monitor in accordance with this invention.

The activity monitor 80 comprises a motion sensor generator 82 to be described in detail relative to FIGS. 3 and 4. The motion sensor generator converts animal motion into electrical energy in the form of voltage pulses. The sensor, therefore, acts as a transducer to transform physical movement of the animal into pulses which are used by the system in the first instance to determine activity. Voltage pulses produced by the generator are filtered by low pass filter 84 to attenuate the pulses produced by the motion sensor and eliminate transients or pulses below a threshold value in the output voltage pulses of the generator 82. The low pass filter output is delivered to a binary counter 86 which records the number of voltage pulses. The buffer 88 acts as a gate between the powered activity monitor 80 and the unpowered transponder 8.

The buffer 88 provides a high impedance load to the counter 86 outputs in either its powered or unpowered states. Thus when the transponder is unpowered no data transfer occurs because the buffer in unpowered and no data transfer to the register occurs.

When the transponder is interrogated and therefore powered the buffer is powered and the data is passed to the transponder registers for transmission via the responder during the interrogation interval. The buffer is necessary because a direct connection from the counter outputs to the shift register inputs would load the counter outputs and drain the activity monitor power supply.

A parallel output of the motion sensor generator 82 is a series of voltage pulses which are converted via the power supply 90 to drive the counter 86. Such is illustrated relative to FIG. 4.

FIG. 4 is a schematic circuit diagram of the activity monitor 80 showing the essential electrical components. The motion sensor/generator 82 is schematically illustrated as a current source having its output coupled to the half wave rectifier formed by diodes $D_1$ and $D_2$. The rectified output is delivered to a capacitor $C_1$ which serves as the power supply for the binary counter 86.

Voltage pulses from the motion sensor/generator 82 are clamped at a value above the capacitor voltage $V_{c1}$, typically approximately 0.7 V. The excess charge is then stored in the capacitor $C_1$ such that the capacitor is continually charged by voltage pulses which are produced by the motion sensor/generator 82.

Diode $D_1$ of the half wave rectifier is a low leakage type to reduce current consumption. Typically, leakage rates are less than 1 pA current consumption at a reverse bias voltage of 5 V. Preferably, the power supply capacitor $C_1$ is a Tantalum type necessary to meet the requirements of this system, that is small size, large capacitance and low leakage (less than 10 pA current at 2.5 V).

The components of FIG. 4 may preferably employ the following components/values: $D_2$-1N914; $D_1$ PAD 1; R 1M $\Omega$; $C_1$ 10 $\mu$F; $C_2$ 5–150 pF. It is understood that such values may be altered depending on the specific mode of implementation and animal involved.

The low pass filter 84 is formed by the RC combination of the resistor R and capacitor $C_2$ shown in FIG. 4. The $RC_2$ low pass filter is used to adjust the sensitivity of the device. Low magnitude pulses may be attenuated if desired so that they are not recorded by the binary counter. Such a feature is potentially advantageous in the detection of estrus.

As illustrated in FIG. 4, the binary counter continually increments until it reaches capacity, at which time it automatically resets at 0 and again commences counting. The binary counter multi-bit output is delivered to the buffer 88. The counter may be a MC 14020 14-stage Ripple Carry Binary Counter (Motorola) and the buffer 88 may be a MC 14050 HEX Non-Inverting Buffer (Motorola). Both devices are commercially available and the choice of a particular product is within the level of ordinary skill.

Referring to FIG. 3, a side view of the motion sensor is depicted with FIG. 3A illustrating the hammer component.

The sensor comprises a beam of piezoelectric material 30 which is supported at both ends by a holding clip 32. The piezoelectric material may be Lead Zirconate Titanate Bimorph, Venitron, PZT-5H (Vernitron Piezoelectric Bedford OH). An epoxy coated lead hammer 34 is positioned at the center portion of the beam. As illustrated in FIG. 3B, the lead hammer comprises a mass which is suspended by spring steel wires 36, the wires being suitably coupled to the housing at points 38 to allow the hammer to swing freely. Animal motion, therefore, causes the hammer to move and strike the beam which in turn generates a potential difference (voltage pulses) between outer plates of the piezoelectric material. By this technique, mechanical energy caused by cow motion is transformed into electrical energy.

As shown in FIG. 3A, a mylar pad 40 is used to absorb the blows caused by the lead hammer 34, yet, at the same time, transmit force to the PZT-5H bimorph material. An epoxy pad may be used on top of the mylar insulator to directly absorb blows from the hammer 34. A stop 44 is provided to prevent excessive deformation of the bimorp. An adhesive, typically RTV may be used to mount the entire assembly onto a substrate 46. The entire unit is formed as one housing integral with the transponder and counter circuitry.

When the animal carrying the activity monitor/transducer passes into the range of an interrogation transmitter/receiver, the power supply in the transponder activates the buffer 88 such that the output from the binary counter 86 is coupled to the transponder encoder through the bit register. Thus, activity information is encoded as a portion of the transponder code word. This code word is shown in FIG. 5 as comprising three segments, a marker segment, an activity segment and an identification segment.

Using the techniques described in the co-pending U.S. patent application Ser. No. 406,471, a transponder return signal is modulated by a twinned binary form of the code word. The return signal is coupled to the receiver via a loop antenna 12.

In accordance with this invention, the output of the receiver 14 is transferred to a data processing unit 20. That processor reads the code word and may either display the identification of the animal and activity information on a real time basis or transfer data to some other display device such as printer monitor or the like. The processor 20 also stores activity data relative to each animal under management who performs those calculations necessary to signal periods of estrus. While the specific programming for the processor 20 to determine the onset of estrus is not set forth herein, such is well known in the art and accordingly is not set forth herein in detail.

FIG. 6 illustrates the placement of the activity monitor/transducer position around the animals' neck via a chain. In this position, the motion sensor will detect movements of the head and neck as well as body movements of sufficient magnitude to swing the activity monitor and, therefore, cause movement of the lead hammer 34. It is apparent that the activity monitor/transducer could be mounted at other positions on the animal or, implanted.

Conventionally, the activity monitor/transducer would be interrogated twice daily at approximately twelve-hour intervals as the cows enter the milking parlor. Given this repetitive interrogation, accurate data from the counter 86 is provided indicative of activity during the preceding twelve hour period.

To characterize the estrus detection performance of the activity monitor, a number of non-pregnant cows were outfitted with neck-mounted activity monitors as illustrated herein. The cows were housed in free stall barns in groups of either 10 or 20 cows per pen. The cows remained in their respective pens for all daily activities with the exception of milking. Milking occurred twice daily at approximately 1:30AM and 1:30PM. The cows used in the study ranged from $1^{st}$ to $5^{th}$ lactation. The number of days from parturition to the monitored estrus period ranged from 33 to 300 days.

The activity monitors were coupled to the Identification Systems as discussed herein in FIGS. 1–2 as disclosed in the co-pending application. The activity monitors were automatically 'read' twice daily as the cows entered the milking parlor. The respective readings were stored in the Random Access Memory of a Kim-1 Microcomputer Module manufactured by MOS Technology, Inc.

Milk samples were collected for each cow at 2 or 3 day intervals. The milk samples were analyzed for progesterone using a solid-phase radioimmunoassay. The milk progesterone levels serve as the standard for determining periods of estrus.

The activity level profiles for the respective cows were individually plotted and combined in FIG. 7. This Figure is the average activity profile for the ten free stall cows for a 2 day pre-estrus and a 2-day post-estrus interval. An increase in activity level was confirmed to be an indication of estrus when it coincided with a low progesterone level (1 ng/ml). For the activity profiles of cows that did not have milk samples taken (3 cows), an increase in activity level was confirmed to be an indication of estrus when it coincided with behavorial signs of estrus (i.e., standing and/or riding). For the individual plots, the activity levels were normalized so that the non-estrus baselines (means=$\overline{X}$) are equal to 1. The non-estrus baselines were calculated by averaging the activity levels over the respective number of readings, excluding the estrus period activity level.

The performance of the activity monitor as a predictor of estrus for the ten free stall cows is given in the following table. For the table, the mean and standard deviation were calculated for each consecutive reading and compared to the next reading. For example, the mean and standard deviation are first calculated for readings 1 and 2 and compared to reading 3. This is followed by calculations for readings 1, 2, and 3 and a comparison to reading 4. This process continues up to the respective estrus activity level reading.

The heat detection rates range from 10% to 90% and the accuracies range from 28% to 100% for the six criteria examined. Of the six criteria, the 2x Mean criteria results in the highest combined heat detection rate (70%) and accuracy (88%). The criteria of Mean+3SD also has reasonable results with a 70% accuracy and a 70% heat detection rate.

| | Activity as a Predictor | | | |
|---|---|---|---|---|
| Criteria | Readings > Criteria | Readings > at Estrus | Heat Det. Rate | Accuracy |
| Mean + 1 SD | 32 | 9 | 90% | 28% |
| Mean + 2 SD | 16 | 7 | 70% | 44% |
| Mean + 3 SD | 10 | 7 | 70% | 70% |
| 2 × Mean | 8 | 7 | 70% | 88% |
| 2 × Mean | 3 | 3 | 30% | 100% |
| 4 × Mean | 1 | 1 | 10% | 100% |

The results, although limited in quantity, indicate that the activity monitor can be used for estrus detection. For the ten cows examined using the pre-estrus and post-estrus data, the heat detection rate is 70% with a 100% accuracy using a criteria that an activity level of 3 standard deviations greater than the baseline mean corresponds to an estrus period. For the analysis using only the pre-estrus data, the heat detection rate is 70% with an 88% accuracy using a criteria of 2X the baseline mean.

While this invention has been disclosed relative to its preferred embodiment, it is apparent that a number of modifications may be practiced without departing from the scope of this invention. For example, the motion sensor may be of an alternative design mounted, for example, on the leg of the animal.

Additionally, as disclosed herein, the activity monitor is self-powered by means of the piezoelectric transducer. With contemporary circuitry such as complementary metal-oxide semiconductor integrated circuit devices (CMOS), circuits can be designed in the extremely low static power requirements. Consequently, once mechanical energy of the activity monitor is converted into electrical energy to continuously power a circuit, elements other than activity for estrus detection are possible.

While the binary counter 86 is coupled directly to the buffer 84, as shown in FIG. 4, other "read" devices could be employed. The counter, for example, could be hard wired directly to a microprocessor or display circuit on the activity monitor. The counter could be interfaced to both passive and active transponders or, interfaced to a transponder without the correlary identification function.

Finally, while the invention has been described relative to the use of a single piezoelectric transducer, it is apparent that multiple transducers could be employed either in a backup capacity or utilizing one as the motion sensor per se and a second for purposes of electrical powered generation.

Having described our invention, we claim:

1. A detection system for an animal comprising:
   a transponder mounted to the animal, said transponder including transducer means responsive to movement of the animal to generate a series of electrical pulses, first circuit means receiving said electrical pulses and generating a count indication of animal movement, second circuit means receiving said electrical pulses and storing electrical energy for driving said first circuit means, and means for storing said count together with an identification code unique to said animal,
   means for interrogating said transponder to receive data therefrom; and
   process means for receiving data from said interrogator means.

2. The detection system of claim 1 wherein said transducer means comprises a piezoelectric member mounted on a base and a suspended mass positioned to move and strike said piezoelectric member in response to movement of said animal.

3. The detection system of claim 2 further comprising an insulator placed on said piezoelectric member to contact said mass and transfer the force of striking by said mass to said piezoelectric member.

4. The detection system of claim 1 wherein said first circuit means comprises a binary counter receiving pulses from transducer and generating a count value and memory means for said count value.

5. The detection system of claim 4 further comprising a low-pass filter interposed between said transducer and said counter.

6. The detection system of claim 1 wherein said second circuit means comprises rectifier means receiving said electrical pulses and producing a rectified output and capacitor means for storing said rectified output.

7. The detection system of claim 6 wherein said first circuit means is coupled to said capacitor and is powered thereby.

8. The detection system of claim 1 wherein said transponder receives an input burst signal at a given frequency from an external source, said transponder further comprising:
   antenna circuit means storing unregulated power from said received input burst signal, means receiving said unregulated power and producing clock pulses of variable period; means for encoding said stored count and said identification code; and modulator means receiving encoded identification and count data from said encode means and producing a modulated signal to said antenna circuit means, wherein said antenna circuit means utilizes said stored power to transmit a coded signal at said frequency.

9. The detection system of claim 8 wherein said means for storing said count together with an identification code comprises a code register programmed and storing said identification code and storing count data from said first circuit means and, said means for encoding receiving said identification code and said stored count from said code register and shaping it into a twin binary signal.

10. The detection system of claim 9 wherein said twin binary signal comprises a marker portion of a predetermined number of bits, an activity portion of a predetermined number of bits and an identification portion of a predetermined number of bits.

11. The detection system of claim 8 wherein said means producing clock pulses produces clock pulses having a period that varies as a function of said unregulated power.

* * * * *